United States Patent [19]

Tamura et al.

[11] Patent Number: 5,059,736

[45] Date of Patent: Oct. 22, 1991

[54] PROCESS FOR PRODUCTION OF SEC-BUTYLBENZENE

[75] Inventors: Mitsuhisa Tamura; Kazuhiro Yamauchi; Yasuhiko Higashio; Kazuteru Takahashi, all of Chiba, Japan

[73] Assignee: Sumitomo Chemical Co., Ltd., Osaka, Japan

[21] Appl. No.: 514,060

[22] Filed: Apr. 24, 1990

[30] Foreign Application Priority Data

Apr. 25, 1989 [JP] Japan .................................. 1-106657
Feb. 27, 1990 [JP] Japan .................................. 2-48849

[51] Int. Cl.$^5$ .............................................. C07C 2/70
[52] U.S. Cl. ...................................... 585/461; 585/459
[58] Field of Search ........................................ 585/461

[56] References Cited

U.S. PATENT DOCUMENTS

| | | | |
|---|---|---|---|
| 2,338,711 | 1/1944 | D'Ouville et al. | 583/461 |
| 3,277,196 | 10/1966 | Winkler | 260/671 |
| 3,448,161 | 6/1969 | Garcia | 585/461 |
| 3,657,148 | 4/1972 | Becker et al. | 585/461 |
| 3,819,735 | 6/1974 | Argento et al. | 585/461 |
| 3,985,819 | 10/1976 | Kobayashi et al. | 585/461 |

FOREIGN PATENT DOCUMENTS 0202526 12/1955 Australia .
0606970 10/1960 Canada .
0711793 7/1954 United Kingdom .
1419270 12/1975 United Kingdom .

Primary Examiner—Patrick P. Garvin
Assistant Examiner—E. O. Irzinski
Attorney, Agent, or Firm—Sughrue, Mion, Zinn Macpeak & Seas

[57] ABSTRACT

A process for production of sec-butylbenzene from benzene and n-butene in the presence of a liquid aluminum chloride complex catalyst is disclosed, wherein the amount of aluminum chloride used as a component of the complex catalyst is from 0.3 to 5 wt % of the benzene used, the reaction temperature is from 20° to 90° C., and the weight ratio of isobutylbenzene formed as a by-product to sec-butylbenzene formed is not more than 0.01:1.

9 Claims, No Drawings

PROCESS FOR PRODUCTION OF SEC-BUTYLBENZENE

FIELD OF THE INVENTION

The present invention relates to a process for production of sec-butylbenzene from benzene and n-butene.

sec-Butylbenzene produced by the present invention is particularly useful for use as a starting material for production of phenol and methyl ethyl ketone through the respective steps of air oxidation and decomposition. Phenol can be used as a starting material for production of synthetic resins and antioxidants, and methyl ethyl ketone can be used as a solvent or for dewaxing of lubricating oils.

BACKGROUND OF THE INVENTION

Use of a liquid aluminum chloride complex catalyst in production of sec-butylbenzene from benzene and n-butene has heretofore been known. For example, JP-A-50-137933 (the term "JP-A" as used herein means an "unexamined published Japanese patent application") discloses a method in which a liquid aluminum chloride complex catalyst is used in such an amount that the amount of aluminum chloride is from 0.05 to 0.25% by weight of the reaction mixture.

In production of sec-butylbenzene from benzene and n-butene by an alkylation method, the product is a mixture mainly containing sec-butylbenzene (SBB), isobutylbenzene (IBB), dibutylbenzenes (DSBB), and tributylbenzenes (TSBB).

Of these compounds, dibutylbenzenes and tributylbenzenes are each separated from the reaction mixture and then transalkylated into sec-butylbenzene. This reaction can be illustrated as follows:

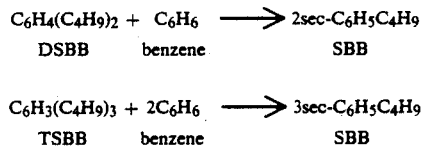

Boiling points of isobutylbenzene and sec-butylbenzene are 172.8° C. and 173.5° C., respectively, and are close to each other. Thus it is difficult to separate these two compounds from each other by distillation. In the production of phenol, Isobutylbenzene formed as a by-product in the above reaction is sent as such to an air oxidation step along with sec-butylbenzene. It is known, however, that if sec-butylbenzene contains isobutylbenzene, the rate of reaction in the air oxidation step is markedly decreased (see JP-A-48-80524). For example, the rate of oxidation of sec-butylbenzene, when the sec-butylbenzene contains 1% by weight of isobutylbenzene, decreases to about 91% of that when the sec-butylbenzene does not contain isobutylbenzene at all. Similarly, when the isobutylbenzene content is 1.65% by weight, the rate of oxidation decreases to about 86%; when the isobutylbenzene content is 2% by weight, the rate of oxidation decreases to about 84%; and when the isobutylbenzene content is 3.5% by weight, the rate of oxidation decreases to as much as about 82%.

Therefore, in order to efficiently undergo the air oxidation step, it is necessary to use sec-butylbenzene having a decreased isobutylbenzene content is possible. For this reason, the amount of isobutylbenzene formed as a by-product at the step of production of sec-butylbenzene from benzene and n-butene should be minimized.

In the conventional alkylation method, however, since the reaction is carried out in a lower aluminum chloride catalyst concentration range, the reaction temperature should be maintained at a high level in order to proceed the reaction sufficiently. In this case, a problem arises in that the amount of isobutylbenzene formed as a by-product reaches to 1 to 4% by weight of sec-butylbenzene formed, and a large amount of isobutylbenzene is inevitably supplied to the air oxidation step.

SUMMARY OF THE INVENTION

The present invention is intended to overcome the above problems, and an object of the present invention is, therefore, to provide a process for production of sec-butylbenzene in a high yield while maintaining the amount of isobutylbenzene formed as a by-product at a low level.

It has now been found that the above object is attained by optimizing the amount of catalyst and the reaction temperature.

The present invention relates to a process for producing sec-butylbenzene from benzene and n-butene in the presence of a liquid aluminum chloride complex catalyst, wherein the amount of aluminum chloride used as a component of the complex catalyst is from 0.3 to 5% by weight of the benzene to be used in the reaction, the reaction temperature is from 20° to 90° C., and the amount of isobutylbenzene formed as a by-product is controlled and limited to not more than 1% by weight of sec-butylbenzene formed.

DETAILED DESCRIPTION OF THE INVENTION

The liquid aluminum chloride complex catalyst (hereinafter referred to as a "complex catalyst") to be used in the present invention refers to a homogeneous complex catalyst, comprising aluminum chloride, hydrogen chloride and an aromatic hydrocarbon. As the aromatic hydrocarbon, sec-butylbenzene, ethylbenzene, di-sec-butylbenzene, and tri-sec-butylbenzene can be used alone or in admixture of two or more thereof. Of these, sec-butylbenzene is most suitable.

In connection with the relative amounts of aluminum chloride, hydrogen chloride and aromatic hydrocarbon, hydrogen chloride and aromatic hydrocarbon are used in amounts of about 1 mole and 2 to 10 mole, respectively, per mole of aluminum chloride.

In preparation of the complex catalyst, it suffices that the above components are mixed and stirred into a homogeneous solution. This is attained by stirring at room temperature for from about 20 minutes to 3 hours. The complex catalyst thus prepared can be used as such in the reaction of benzene and n-butene.

The complex catalyst, after once used in the reaction, can be separated from the reaction mixture and reused another the reaction.

n-Butene to be used in the present invention includes 1-butene, cis-2-butene, and trans-2-butene. In addition, mixtures of the above compounds can be used, and mixtures of n-butene and compounds inert to the reaction, such as butane, ca be used.

In production of sec-butylbenzene from benzene and n-butene according to the process of the present invention, benzene, n-butene and the above complex catalyst are mixed and stirred.

The amount of n-butene used is preferably from 0.1 to 1.2 mole, more preferably from 0.4 to 1.1 mole, per mole of benzene. If the amount of n-butene used is too small, the volume efficiency of the reaction is decreased, and the cost for separation of sec-butylbenzene from the reaction mixture is increased. On the other hand, if the amount of n-butene used is too large, the concentration of alkylbenzene by-products having two or more butyl groups undesirably increases.

In connection with the amount of the complex catalyst used, the amount of aluminum chloride in the complex catalyst is from 0.3 to 5% by weight, more preferably from 0.3 to 1% by weight, based on the amount of benzene used in the reaction. If the amount of the complex catalyst used is less than the above specified range, the reaction must be carried out at elevated temperatures in order to proceed the reaction sufficiently. In this case, formation of an undesired by-product, isobutylbenzene increases. On the other hand, if the amount of the complex catalyst used is in excess of the above specified range, the catalyst cost is undesirably increased. Also, in this case, formation of undesired the by-product, isobutylbenzene, is increased.

The reaction temperature is from 20° to 90° C., preferably from 20° to 70° C. In the case that the reaction temperature is higher than this range, formation of isobutylbenzene increases. On the other hand, in the case that the reaction temperature is lower than the above-specified range, the reaction for formation of sec-butylbenzene does not proceed to completion. In this case, if in order to thoroughly proceed the reaction the amount of the catalyst used is increased, formation of isobutylbenzene undesirably increases.

The most significant characteristic of the present invention is that, by setting up an optimum combination of a relatively low reaction temperature with a relatively high amount of the catalyst as compared with those in the conventional techniques, not only formation of undesirable by-products is inhibited, but the desired reaction can proceed to completion.

The reaction pressure is not critical.

The amount of isobutylbenzene formed as a by-product, in the reaction mixture obtained by the present invention can be maintained at not more than 1%, preferably not more than 0.8%, by weight of sec-butylbenzene formed. The significance in maintaining the ratio of isobutylbenzene to sec-butylbenzene formed at a low level is as described hereinbefore.

The present reaction can be carried out batchwise or continuously.

Separation and recovery of sec-butylbenzene from the reaction mixture obtained in the reaction of benzene and n-butene in the present invention can be carried out by the usual techniques. For example, after separation of the complex catalyst from the reaction mixture by a liquid-separating operation, or without separation of the complex catalyst from the reaction mixture, the reaction mixture is washed with water to inactivate the complex catalyst. After removal of the inactivated complex catalyst the residue is further washed with an aqueous sodium hydroxide solution to remove the complex catalyst completely, and then separated into an oil layer and an aqueous layer. Then, the oil layer thus obtained is distilled into a fraction mainly containing sec-butylbenzene, a fraction mainly containing dibutylbenzenes and tributylbenzenes, a fraction mainly containing heavy materials, and a fraction mainly containing unreacted benzene. Thereafter, if desired, the fraction containing dibutylbenzenes and tributylbenzenes is recycled to the aforementioned transalkylation, step where they are converted into sec-butylbenzene. The unreacted benzene is returned to the step where sec-butylbenzene is produced from benzene and n-butene.

It is also preferred that along with the above separated benzene, the fraction mainly containing dibutylbenzenes and tributylbenzenes is returned to the reaction zone of benzene and n-butene.

It is further preferred that the complex catalyst used in the reaction is, after completion of the reaction, separated and recovered from the reaction mixture by the liquid-separating operation, and the complex catalyst thus separated is recycled to the reaction zone of benzene and n-butene.

sec-Butylbenzene obtained by the process of the present invention can be suitably used as a starting material for production of phenol. A method of production of phenol from sec-butylbenzene is described in, for example, JP-A-48-80524. That is, sec-butylbenzene is oxidized into sec-butylbenzene hydroperoxide at from about 75° to 140° C. Then the sec-butylbenzene hydroperoxide is concentrated and decomposed with an acid catalyst to produce phenol and methyl ethyl ketone.

In accordance with the present invention, as described above, a process for production of sec-butylbenzene from benzene and n-butene can be provided, which maintains the ratio of isobutylbenzene to sec-butylbenzene formed at a low level and sufficiently increases the extent of the reaction.

The present invention is described in greater detail with reference to the following examples, although it is not intended to be limited thereto.

EXAMPLE 1

61.64 g of sec-butylbenzene and 26.79 g of aluminum chloride were placed in a 200-milliliter three-necked flask equipped with a stirrer and a gas inlet tube. Through the gas inlet tube, hydrogen chloride gas was blown over 2 hours while stirring. With a lapse of time, aluminum chloride was dissolved in sec-butylbenzene, and as a uniform solution, a liquid aluminum chloride complex catalyst (95 g, aluminum chloride concentration: 28 wt%) was obtained.

Separately, 78 g (1 mole) of benzene and 1.43 g (3.0 mmole) of the above complex catalyst were placed in a 200-milliliter three-necked flask equipped with a stirrer and a gas inlet tube. With stirring and while controlling the flow rate with a mass flow controller, 1-butene was blown through the gas inlet tube over 1 hour at a rate of 1 mole/hr. During the time, the flask was cooled on a water bath, and the reaction temperature was controlled at 36° C. After completion of the reaction, the reaction mixture was cooled to room temperature, and the reaction mixture was taken out of the flask, washed with 30 g of a 30 wt% aqueous sodium hydroxide solution to inactivate the catalyst, and then liquid-separated. Then, the reaction mixture was analyzed by gas chromatography under the conditions shown below to determine the composition. The results are shown in Table 2. Analytical Conditions
Column: DB-1 capillary column, 60 m
Temperature: Maintained at 100° C. for 10 minutes, and raised from 100° C. to 200° C. at a rate of 10° C./min.

EXAMPLES 2 TO 5

The procedures of Example 1 were repeated with the exception that the amount of the complex catalyst and the reaction temperature were changed as shown in Table 2. The results are shown in Table 2.

EXAMPLE 6

The procedures of Example 1 were repeated with the exception that the amount of the complex catalyst and the reaction temperature were changed a shown in Table 2 and that a mixed butene shown in Table 1 was used in place of 1-butene. The results are shown in Table 2.

The total amount of 1-butene, cis-2-butene and trans-2-butene used was 1 mole.

TABLE 1

| Composition of Mixed Butene | |
|---|---|
| Component | wt % |
| 1-Butene | 4.47 |
| Cis-2-butene | 17.62 |
| Trans-2-butene | 27.13 |
| Isobutylene | 0.012 |
| Butane | 50.69 |

COMPARATIVE EXAMPLES 1 AND 2

The procedures of Example 1 were repeated with the exception that the amount of the complex catalyst and the reaction temperature were changed as shown in Table 2. The results are shown in Table 2.

EXAMPLE 7

78 g (1 mole) of benzene and 1.43 g (3.0 mmole) of the same complex catalyst as used in Example 1 were placed in a 200-milliliter three-necked flask equipped with a stirrer and a gas inlet tube. With stirring under atmospheric pressure and while controlling the flow rate with a mass flow controller, 1-butene was blown through the gas inlet tube at a rate of 0.67 mole/hr over 1 hour at a reaction temperature of 50° C. After completion of the blowing, stirring was carried out at 50° C. over 30 minutes. After the reaction was completed, the reaction mixture was cooled to room temperature, taken out of the flask, washed with 30 g of a 30 wt% aqueous sodium hydroxide solution to inactivate the catalyst, and then separated. The composition of the reaction mixture was analyzed by gas chromatography. The results are shown in Table 2.

EXAMPLE 8

Assuming that dibutylbenzenes separated from the reaction mixture is recycled, the reaction was carried out as follows.

339.0 g (4.34 mole) of benzene, 50.6 g (0.27 mole) of di-sec-butylbenzene and 6.59 g (0.0138 mole) of a complex catalyst were placed in a 1-liter three-necked flask equipped with a stirrer and a gas inlet tube. Under atmospheric pressure, with stirring, and at a reaction temperature of 66° C., 1-butene was blown through the gas inlet tube at a flow rate of 1.81 mole/hr for 1 hour. After completion of the blowing, stirring was carried out at 66° C. for 4 hours. After completion of the reaction, workup and analysis were carried out in the same manner as in Example 1.

Composition of Reaction Mixture:

Benzene: 39.81 wt %; SBB: 47.28 wt %; IBB: 0.39 wt %;

DSBB: 10.76 wt %; TSBB: 0.53 wt %

Benzene Conversion: 41.6%

$$SBB \text{ Selectivity} = \frac{\text{Formed } SBB \text{ (mole)}}{\text{Reacted Benzene (mole)} + \text{Reacted } DSBB \text{ (mole)} + \text{Reacted } TSBB \text{ (mole)}} = 98.7\%$$

IBB/SBB = 0.0083

TBB/SBB = 0

In all the examples in which the reaction was carried out with the proper amount of the complex catalyst and reaction temperature as specified in the present invention, the reaction proceeded sufficiently (benzene conversion was high), the concentration of the undesired by-product, isobutylbenzene, was lower, and the objects of the present invention were sufficiently achieved.

On the other hand, in Comparative Example 1 in which the amount of the complex catalyst was less than the range specified in the present invention, the reaction proceeded insufficiently (benzene conversion was low). Also, in Comparative Example 2 in which the amount of the complex catalyst was outside the range specified in the present invention, an excess of the undesired by-product, isobutylbenzene, was formed.

TABLE 2

| | Reaction Conditions and Reaction Results | | | | | | | | |
|---|---|---|---|---|---|---|---|---|---|
| | Example No. | | | | | | | Comparative Example No. | |
| | 1 | 2 | 3 | 4 | 5 | 6 | 7 | 1 | 2 |
| Amount of Complex Catalyst (AlCl$_3$/benzene) (wt %) | 0.51 | 0.85 | 1.71 | 0.51 | 0.51 | 1.71 | 0.51 | 0.10 | 5.10 |
| Benzene/n-Butene Ratio (molar ratio) | 1:1 | 1:1 | 1:1 | 1:1 | 1:1 | 1:1 | 1:0.67 | 1:1 | 1:1 |
| Reaction Temperature (°C.) | 36 | 33 | 33 | 80 | 53 | 30 | 50 | 63 | 32 |
| Composition of Reaction Product | | | | | | | | | |
| Benzene (wt %) | 24.53 | 23.87 | 20.34 | 20.81 | 22.42 | 27.01 | 29.26 | 99.70 | 22.60 |
| SBB[1] (wt %) | 25.81 | 27.35 | 31.26 | 35.41 | 28.95 | 27.94 | 52.70 | 0.13 | 35.23 |
| IBB[2] (wt ppm) | 304 | 433 | 1303 | 3200 | 547 | 598 | 1693 | 11 | 6024 |
| TBB[3] (wt ppm) | 83 | 58 | 27 | 53 | 80 | 116 | 0 | 0 | 0 |
| DSBB[4] (wt %) | 36.82 | 36.35 | 36.98 | 37.53 | 38.42 | 32.95 | 16.68 | 0.09 | 32.95 |
| TSBB[5] (wt %) | 12.81 | 12.39 | 11.29 | 5.94 | 10.15 | 12.03 | 0.71 | 0.08 | 8.63 |
| Reaction Results | | | | | | | | | |
| Benzene Conversion[6] (%) | 58.2 | 59.3 | 67.5 | 64.7 | 61.5 | 55.4 | 56.2 | 0.1 | 62.1 |

TABLE 2-continued

| | Reaction Conditions and Reaction Results | | | | | | | | |
|---|---|---|---|---|---|---|---|---|---|
| | Example No. | | | | | | | Comparative Example No. | |
| | 1 | 2 | 3 | 4 | 5 | 6 | 7 | 1 | 2 |
| SBB Selectivity[7] (%) | 44.0 | 45.8 | 49.2 | 54.1 | 47.0 | 48.4 | 80.7 | 48.6 | 55.3 |
| IBB/SBB (wt ratio) | 0.0012 | 0.0016 | 0.0042 | 0.0090 | 0.0019 | 0.0021 | 0.0032 | 0.0085 | 0.0171 |
| TBB/SBB (wt ratio) | 0.00032 | -0.00021 | 0.00009 | 0.00015 | 0.00028 | 0.00041 | 0 | 0 | 0 |

[1] SBB: sec-butylbenzene
[2] IBB: isobutylbenzene
[3] TBB: tert-butylbenzene
[4] DSBB: dibutylbenzene
[5] TSBB: tributylbenzene
[6] Benzene conversion = reacted benzene (mole)/benzene used (mole) × 100
[7] SBB selectivity = formed SBB (mole)/reacted benzene (mole) × 100

While the invention has been described in detail and with reference to specific embodiments thereof, it will be apparent to one skilled in the art that various changes and modifications can be made therein without departing from the spirit and scope thereof.

What is claimed is:

1. A process for producing sec-butylbenzene from benzene and n-butene, comprising reacting benzene and n-butene in the presence of a homogeneous liquid aluminum chloride complex catalyst said catalyst comprising aluminum chloride, hydrogen chloride, and an aromatic hydrocarbon, wherein the amount of aluminum chloride used as a component of the complex catalyst is from 0.51 to 5% by weight of the benzene used, the reaction temperature is from 20° to 70° C., and the amount of isobutylbenzene formed as a by-product is such that the weight ratio of isobutylbenzene to sec-butylbenzene formed is not more than 0.01:1.

2. The process as claimed in claim 1, wherein the amount of aluminum chloride used as a component of the complex catalyst is from 0.51 to 1% by weight of the benzene used.

3. The process as claimed in claim 1, wherein the molar ratio of benzene to n-butene to be reacted is from 1 : 0.1 to 1 : 1.2.

4. The process as claimed in claim 3, wherein the molar ratio of benzene to n-butene to be reacted is from 1 : 0.4 to 1 : 1.1.

5. The process as claimed in claim 1, wherein a reaction mixture obtained by reacting benzene and n-butene by the method of claim 1 is separated into a fraction containing mainly benzene, a fraction containing mainly sec-butylbenzene, a fraction containing mainly dibutylbenzenes and tributylbenzenes, and a fraction containing mainly heavy materials, and the fraction containing mainly benzene and the fraction containing mainly dibutylbenzenes and tributylbenzenes are recycled to the reaction zone of claim 1.

6. The process as claimed in claim 1; wherein the amount of isobutylbenzene formed as a by-product is such that the weight ratio of isobutylbenzene to sec-butylbenzene formed is not more than 0.008:1.

7. The process as claimed in claim 1 wherein said aromatic hydrocarbon is selected from the group consisting of sec-butylbenzene, ethylbenzene, di-sec-butylbenzene, tri-sec-butylbenzene and mixtures thereof.

8. The process as claimed in claim 1 wherein said catalyst comprises 1 mole of hydrogen chloride and 2-10 moles of aromatic hydrocarbon, respectively, per mole of aluminum chloride.

9. The process as claimed in claim 1 wherein n-butene includes 1-butene, cis-2-butene, trans-2-butene and mixtures thereof, and mixtures of n-butene with compounds inert to the reaction.

* * * * *